United States Patent
Pham et al.

[11] Patent Number: 5,911,731
[45] Date of Patent: Jun. 15, 1999

[54] ANATOMICALLY SHAPED VASOOCCLUSIVE DEVICES

[75] Inventors: Pete Phong Pham, Fremont; Hong Doan, Santa Clara, both of Calif.

[73] Assignee: Target Therapeutics, Inc., Fremont, Calif.

[21] Appl. No.: 08/949,066

[22] Filed: Oct. 10, 1997

Related U.S. Application Data

[60] Division of application No. 08/536,624, Sep. 29, 1995, which is a continuation-in-part of application No. 08/425,106, Apr. 20, 1995.

[51] Int. Cl.[6] ................................................. A61B 17/12
[52] U.S. Cl. .......................... 606/191; 606/198; 140/92.1
[58] Field of Search ................................... 606/191, 198, 606/200; 623/1, 12, 901; 140/89, 92.1

[56] References Cited

U.S. PATENT DOCUMENTS

| | | | |
|---|---|---|---|
| 3,174,851 | 3/1965 | Buehler et al. | 148/426 |
| 3,351,463 | 11/1967 | Rozner et al. | 148/426 |
| 3,753,700 | 8/1973 | Harrison et al. | 148/402 |
| 4,994,069 | 2/1991 | Ritchart et al. | 606/191 |
| 5,108,407 | 4/1992 | Geremia et al. | 606/108 |
| 5,122,136 | 6/1992 | Guglielmi et al. | 606/32 |
| 5,226,911 | 7/1993 | Chee et al. | 606/191 |
| 5,234,437 | 8/1993 | Sepetka | 606/108 |
| 5,250,071 | 10/1993 | Palermo | 606/198 |
| 5,261,916 | 11/1993 | Engelson | 606/108 |
| 5,304,194 | 4/1994 | Chee et al. | 606/32 |
| 5,304,195 | 4/1994 | Twyford, Jr. et al. | 606/191 |
| 5,312,415 | 5/1994 | Palermo | 606/108 |
| 5,350,397 | 9/1994 | Palermo et al. | 606/200 |
| 5,354,295 | 10/1994 | Guglielmi et al. | 606/32 |
| 5,382,259 | 1/1995 | Phelps et al. | 606/151 |
| 5,423,849 | 6/1995 | Engelson et al. | 606/191 |
| 5,645,558 | 7/1997 | Horton | 606/191 |
| 5,690,666 | 11/1997 | Berenstein et al. | 606/191 |

FOREIGN PATENT DOCUMENTS

| | | |
|---|---|---|
| 0743047 | 11/1996 | European Pat. Off. . |
| 3203410 | 11/1982 | Germany . |
| 9205797 | 6/1992 | Germany . |
| WO 95/12367 | 5/1995 | WIPO . |
| WO 95/25480 | 9/1995 | WIPO . |

*Primary Examiner*—Michael Buiz
*Assistant Examiner*—David O. Reip
*Attorney, Agent, or Firm*—Morrison & Foerster LLP

[57] ABSTRACT

This is a vasoocclusive device which, as used, is in the approximate shape of an anatomical cavity. It may be deployed as a sphere, an ovoid, or other distorted spherical shape. The device is a self-forming shape made from a pre-formed vasoocclusion member. Prior to deployment, the vasoocclusive device is sufficiently straight that it is able to be pushed from a vascular catheter without excessive friction. The vasoocclusion member may be a small helical coil or braid variously comprising a suitable metal, or, in the case of a braid, such metal may be co-woven with various polymeric or natural fibers. Fibers may be introduced onto the device and affixed to the member. The constituent member may be also be covered with a fibrous braid. The device is typically introduced through a catheter. The device is passed axially through the catheter sheath and assumes its form upon exiting the catheter without further action. The invention also includes methods of winding the anatomically shaped vasoocclusive device into appropriately shaped forms and annealing them to form various devices.

28 Claims, 7 Drawing Sheets

Fig. 11 ically SHAPED
VASOOCCLUSIVE DEVICES

This application is a division of application Ser. No. 08/536,624, filed Sep. 29, 1995, now pending; which is a continuation-in-part of patent application Ser. No. 08/425,106 filed Apr. 20, 1995 entitled "Anatomically Shaped Vasoocclusive Device And Method Of Making Same", the entirely of which are incorporated by reference.

FIELD OF THE INVENTION

This invention is a vasoocclusive device. More particularly, it is a vasoocclusive device which, as used, is in the approximate shape of an anatomical cavity. It may be ultimately deployed as a sphere, an ovoid, or other distorted spherical shape. The device is a self-forming shape made from a pre-formed vasoocclusion member. Prior to deployment, the vasoocclusive device is sufficiently straight that it is able to be pushed from a vascular catheter without excessive friction. The vasoocclusion member may be a small helical coil or braid variously comprising a suitable metal, or, in the case of a braid, such metal may be co-woven with various polymeric or natural fibers. Fibers may be introduced onto the device and affixed to the member. The constituent member may be also be covered with a fibrous braid. The device is typically introduced through a catheter. The device is passed axially through the catheter sheath and assumes its form upon exiting the catheter without further action. The invention also includes methods of winding the anatomically shaped vasoocclusive device into appropriately shaped forms and annealing them to form various devices.

BACKGROUND OF THE INVENTION

Vasoocclusion devices are surgical implements or implants that are placed within the vasculature of the human body, typically via a catheter, either to block the flow of blood through a vessel making up that portion of the vasculature through the formation of an embolus or to form such an embolus within an aneurysm stemming from the vessel. One widely used vasoocclusive device is a helical wire coil having windings which may be dimensioned to engage the walls of the vessels. Other less stiff helically coiled devices have been described, as well as those involving woven braids.

For instance, U.S. Pat. No. 4,994,069, to Ritchart et al., describes a vasoocclusive coil that assumes a linear helical configuration when stretched and a folded, convoluted configuration when relaxed. The stretched condition is used in placing the coil at the desired site (by its passage through the catheter) and the coil assumes a relaxed configuration—which is better suited to occlude the vessel—once the device is so placed. Ritchart et al. describes a variety of shapes. The secondary shapes of the disclosed coils include "flower" shapes and double vortices. A random shape is described, as well.

Vasoocclusive coils having attached fibrous elements in a variety of secondary shapes are shown in U.S. Pat. No. 5,304,194, to Chee et al. Chee et al. describes a helically wound device having a secondary shape in which the fibrous elements extend in a sinusoidal fashion down the length of the coil. These coils, as with Ritchart et al., are produced in such a way that they will pass through the lumen of a catheter in a generally straight configuration and, when released from the catheter, form a relaxed or folded shape in the lumen or cavity chosen within the human body. The fibrous elements shown in Chee et al. enhance the ability of the coil to fill space within the vasculature and to facilitate formation of embolus and subsequent allied tissue.

There are a variety of ways of discharging shaped coils and linear coils into the human vasculature. In addition to those patents which apparently describe only the physical pushing of a coil out into the vasculature (e.g., Ritchart et al.), there are a number of other ways to release the coil at a specifically chosen time and site. U.S. Pat. No. 5,354,295 and its parent, 5,122,136, both to Guglielmi et al., describe an electrolytically detachable embolic device.

A variety of mechanically detachable devices are also known. For instance, U.S. Pat. No. 5,234,437, to Sepetka, shows a method of unscrewing a helically wound coil from a pusher having interlocking surfaces. U.S. Pat. No. 5,250,071, to Palermo, shows an embolic coil assembly using interlocking clasps mounted both on the pusher and on the embolic coil. U.S. Pat. No. 5,261,916, to Engelson, shows a detachable pusher-vasoocclusive coil assembly having an interlocking ball and keyway-type coupling. U.S. Pat. No. 5,304,195, to Twyford et al., shows a pusher-vasoocclusive coil assembly having an affixed, approximately extending wire carrying a ball on its proximal end and a pusher having a similar end. The two ends are interlocked and disengage when expelled from the distal tip of the catheter. U.S. Pat. No. 5,312,415, to Palermo, also shows a method for discharging numerous coils from a single pusher by use of a guidewire which has a section capable of interconnecting with the interior of the helically wound coil. U.S. Pat. No. 5,350,397, to Palermo et al., shows a pusher having a throat at its distal end and a pusher through its axis. The pusher sheath will hold onto the end of an embolic coil and will then be released upon pushing the axially placed pusher. wire against the member found on the proximal end of the vasoocclusive coil.

Vasoocclusive coils having little or no inherent secondary shape have also been described. For instance, in U.S. patent application 07/978,320, filed Nov. 18, 1992, entitled "Ultrasoft Embolization Coils with Fluid-Like Properties" by Berenstein et al., is found a coil having little or no shape after introduction into the vascular space.

Common to all of these devices described above is the characteristic of lacking a spheroid shape when relaxed.

SUMMARY OF THE INVENTION

This invention is a vasoocclusive device comprising one or more vasoocclusive members which are wound to form a generally spherical or ovoid shape when relaxed. The vasoocclusive member itself may be a helically wound coil or braid typically comprising a biocompatible metal. Fibrous materials may be woven into the member or tied or wrapped onto it. Desirably, the device is of a size and shape suitable for fitting snugly within a vascular cavity (e.g., an aneurysm, or perhaps, a fistula).

The device may be made in a variety of ways. Typically, the member is helically wound (if a coil) or braided in a generally linear fashion. After completion of that step, it is then wound around an appropriately shaped mandrel or form and heat-treated in such a fashion that it will retain its shape after removal from the heating form. Auxiliary fibrous materials are then added by weaving, tying, or by other suitable permanent attachment methods.

The device is used simply by temporarily straightening the device and introducing it into a suitable catheter, the catheter already having been situated so that its distal opening is within the mouth of the vascular crevice or opening to be filled. The device is then pushed through the catheter and, upon its emanation at the distal end of the catheter into the vascular cavity, assumes its relaxed shape.

DESCRIPTION OF THE INVENTION

Figure 1:
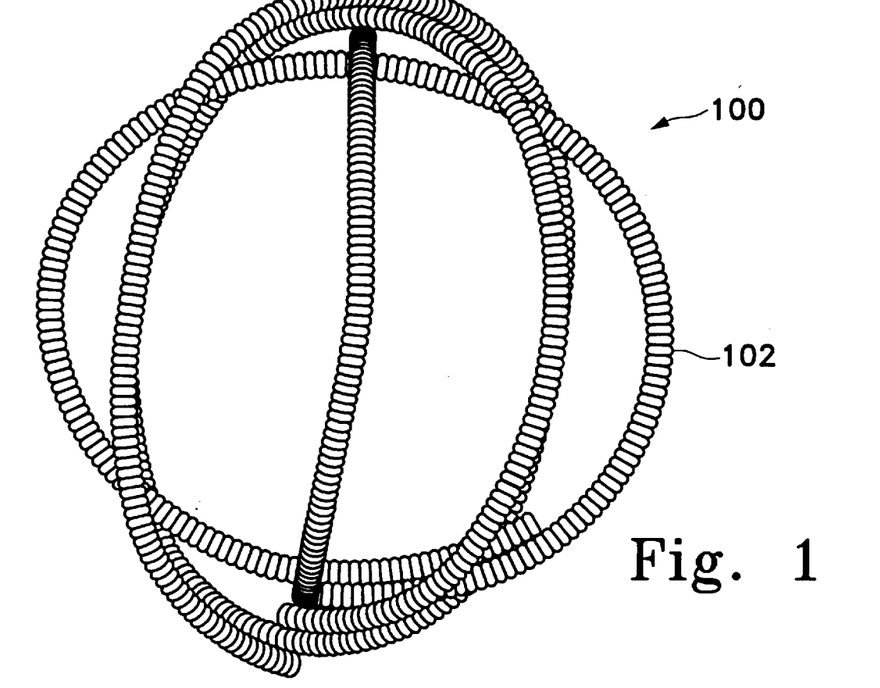
FIG. 1 shows a side view of a spherical device made according to the invention using a helical coil.

FIG. 1 shows one highly desirable variation of this invention—a spherical coil (100). The variation shown is simple in that it has a helically wound coil or vasoocclusive member (102). The vasoocclusion coil (102) has been wound in a cage-like structure so to have eight arms spaced generally equally about the sphere. It is clearly not necessary that the coil secondary shape be precisely spaced around the exterior of the spherical shape (100), but it is desirable from a mechanical point of view that such a spacing be approached. That is to say that the shape of the coil (100) is better maintained within the anatomical cavity when the coil hoop stress is equally maintained against the cavity wall.

Figure 2:
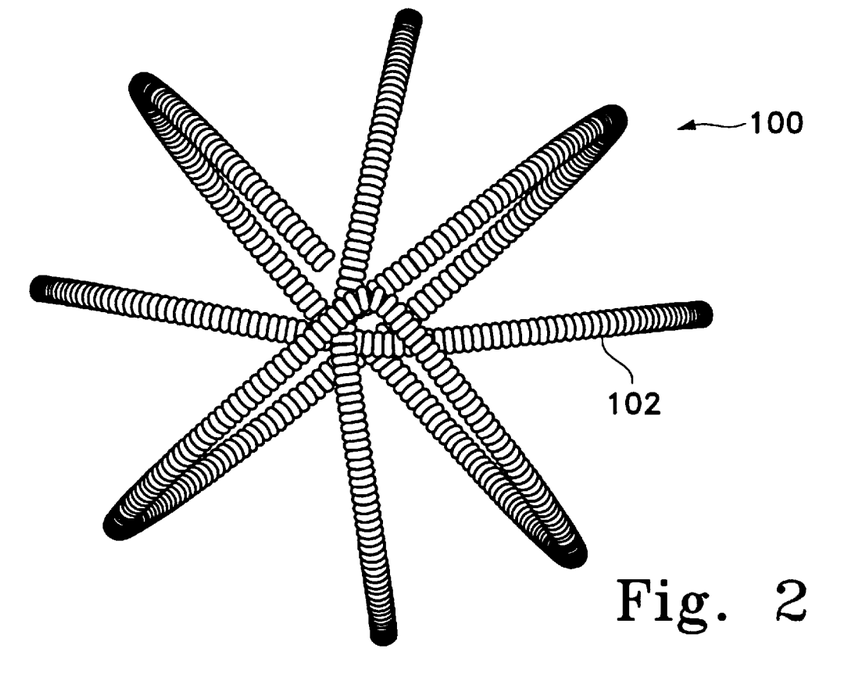
FIG. 2 shows a top view of the device shown in FIG. 1.

FIG. 2 shows a top view of the spherical coil (100) shown in FIG. 1. FIG. 2 depicts the regular spacing of the single coil member (102) wound to form the inventive device. Although the FIG. 1 and FIG. 2 variations show the resulting pattern of wrapping for coil (102) to be fairly regular and forming two opposing "poles" on the device, clearly such is not necessary. It is our intent only that the coil member (102) be in a cage-like structure where at least 90–95% of the coil is in the outer 10–15% of the diameter of the device (100). Somewhat more random placement of coil (100) is permissible and, in many instances, even desired.

As will be discussed below, the manner of wrapping the coil about the shape-producing mandrel is somewhat important to the ultimate operation of the device during deployment. The magnitude of the various bends placed in the primary shape of the coil in producing the secondary shape must not be so acute as to result in excessive resistance against the catheter wall during deployment. In particular, we have found that bends in the primary coil form which are greater than about 135° often cause "pushing" resistance levels which are unacceptable. Primary coil bends of about 45° or greater, e.g., of 135° and 90°, are acceptable in this invention. Bends of 45°, 90°, and 135° are shown in FIG. 2. Furthermore, lack of thought in selecting the appropriate number of loops and the relative magnitude of the sequential bend selection will result in a coil which does not result in a sustainable spherical shape. For instance, we found that a bend sequence of 90°, 90°, 45° resulted in a coil which would not retain a spherical secondary shape after deployment.

The material used in vasoocclusive member (102) may be any of a wide variety of materials; preferably, the wire is a radiopaque material such as a metal or a polymer. Suitable metals and alloys for the wiring include Platinum Group metals, especially platinum, rhodium, palladium, as well as tungsten, gold, silver, tantalum, and alloys of these metals. Highly preferred is a platinum/tungsten alloy.

The wire may also be of any of a stainless steel if some sacrifice of radiopacity may be tolerated. Very desirable materials of construction, from a mechanical point of view, are materials which maintain their shape despite being subjected to high stress. Certain "superelastic alloys" include nickel/titanium alloys (48–58 atomic % nickel and optionally containing modest amounts of iron); copper/zinc alloys (38–42 weight % zinc); copper/zinc alloys containing 1–10 weight % of beryllium, silicon, tin, aluminum, or gallium; or nickel/aluminum alloys (36–38 atomic % aluminum). Particularly preferred are the alloys described in U.S. Pat. Nos. 3,174,851; 3,351,463; and 3,753,700. Especially preferred is the titanium/nickel alloy known as "nitinol". These are very sturdy alloys which will tolerate significant flexing without deformation even when used as a very small diameter wire.

The coils may be made of radiolucent fibers or polymers (or metallic threads coated with radiolucent or radiopaque fibers) such as polyesters (e.g., DACRON), polyglycolic acid, polylactic acid, fluoropolymers (polytetrafluoroethylene or TEFLON), polyamides (e.g., NYLON's), or even silk. Should a polymer be used as the major component of the vasoocclusive member (100), it is desirably filled with some amount of a radiopaque material such as powdered tantalum, powdered tungsten, bismuth oxide, barium sulfate, and the like.

Generally speaking, when the device (100) is formed of a metallic coil as the vasoocclusive member (102) and that coil is platinum or a superelastic alloy such as nitinol, the diameter of the wire used in the is production of the coil will be in the range of 0.0005 and 0.006 inches. The wire of such diameter is typically then wound into a coil having a primary diameter of between 0.005 and 0.018 inches. The preferable diameter is 0.010 to 0.018 inches. We have generally found that the wire should be of sufficient diameter to provide a hoop strength to the resulting device sufficient to hold the device in place within the chosen body cavity without distending the wall of the cavity and without moving from the cavity as a result of the repetitive fluid pulsing found in the vascular system.

Obviously, should a superelastic alloy such as nitinol be used, the diameter of the coil wire may be significantly smaller than that used when the relatively ductile platinum or platinum/tungsten alloy is used as the material of construction.

Finally, as regards FIG. 1, we have found that the overall diameter of the device (100) desirably is between 3 and 12 millimeters. Most aneurysms within the cranial vasculature can be treated by one or more devices having those diameters.

Figure 3:
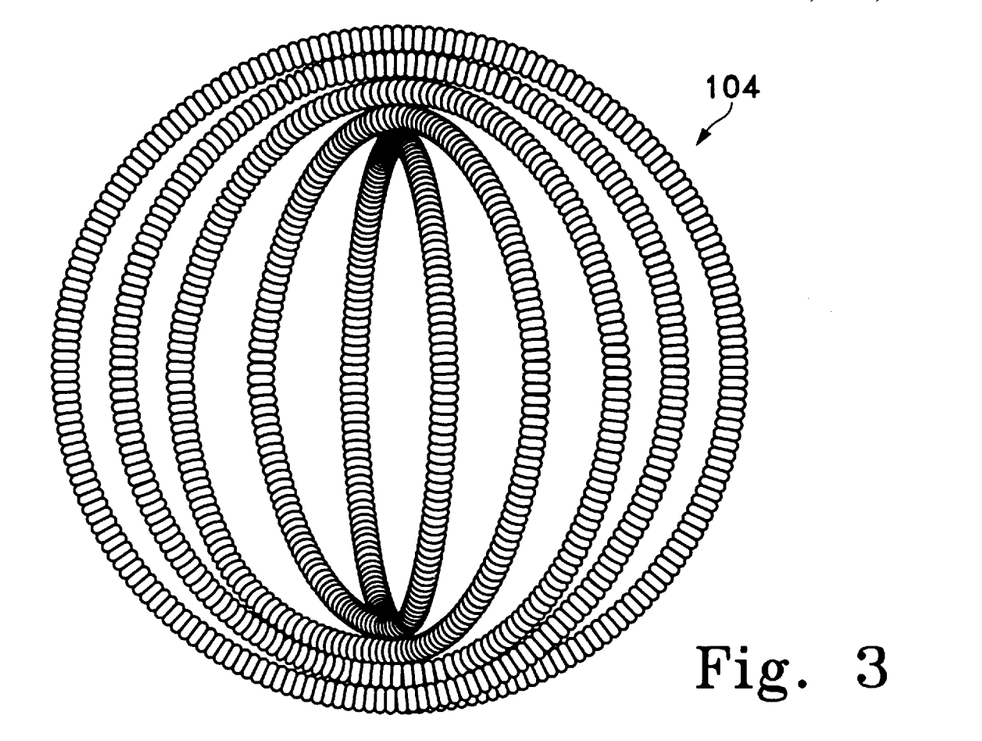
FIG. 3 shows a side view of a device having an oval cross-section made according to the invention.

FIG. 3 shows a variation of the invention in side view in which the shape of the anatomically conforming vasoocclusive device is oval or egg-shaped. Other than the final shape of device (104), the FIG. 3 device is similar to that shown in FIG. 1. It is of little importance which axis of the ovoid structure (104) is the major axis and which is the minor axis. In general, it is desirable that the device be constructed in such a way that the resulting relaxed device have a shape similar to the cavity into which it is placed.

Figure 4:
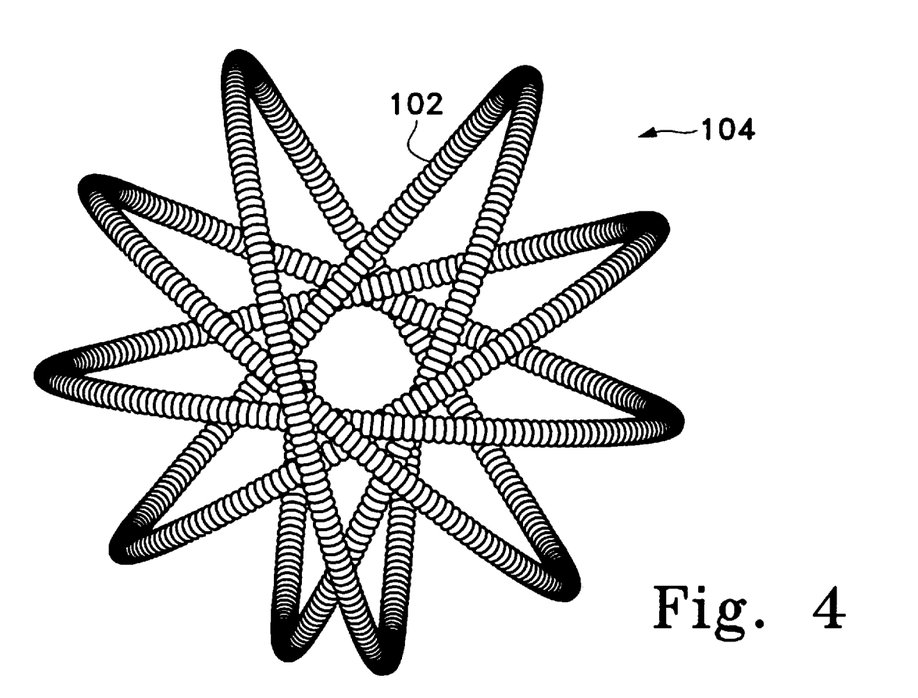
FIG. 4 shows a top view of the device shown in FIG. 3.

FIG. 4 shows a top view of the device shown in FIG. 3. Again, as was discussed above, the device need not have its constituent vasoocclusive members (102) wound as regularly as is shown in FIG. 4. The configuration of the winding may be somewhat more random but should still conform to the parameter that at least 90% of the mass of the member should be within the outer 10–15% of the relaxed (104) shape.

Figure 5:
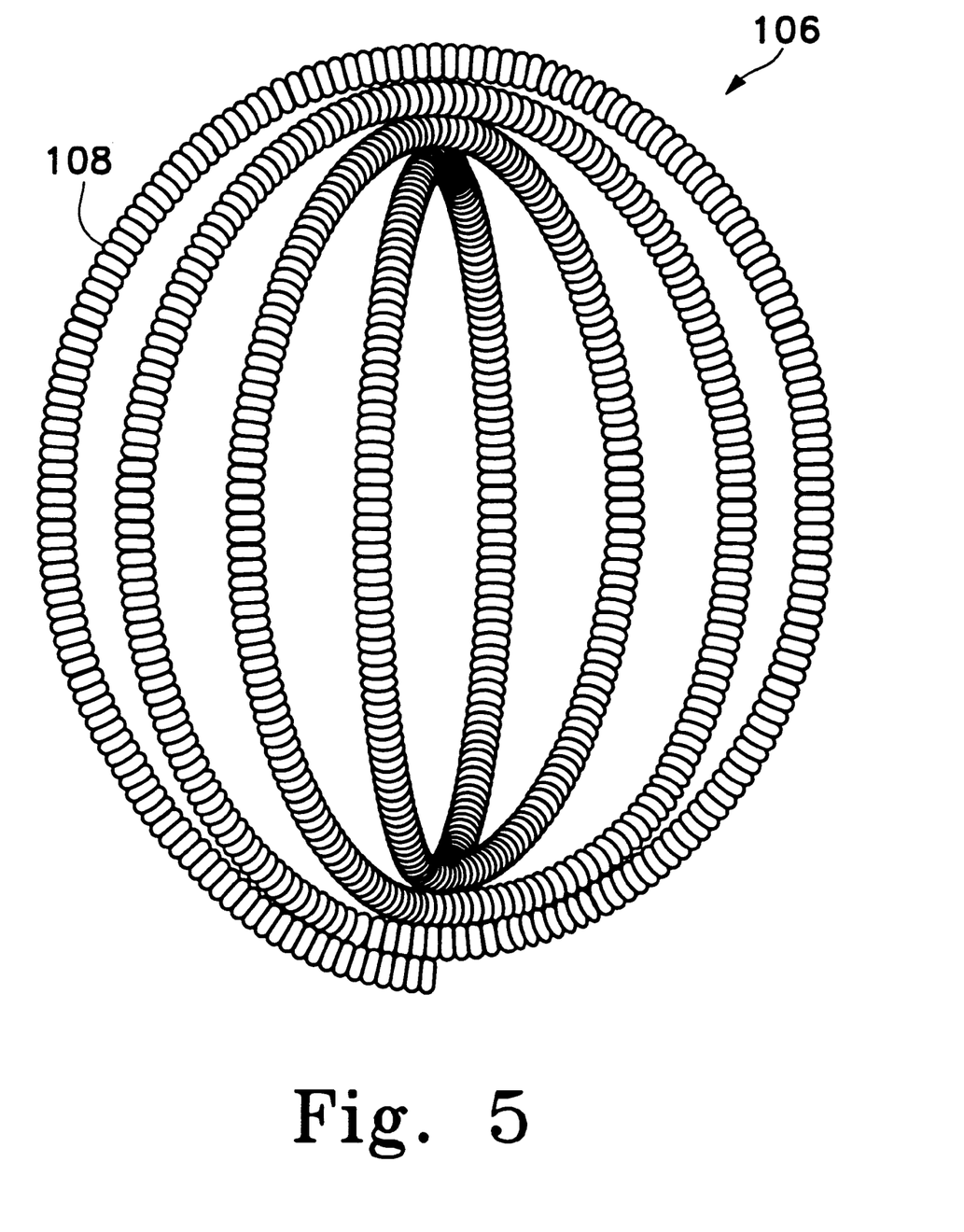
FIG. 5 shows a side view of a device made according to the invention using a braided member.

FIG. 5 shows another variation of the inventive device in which the device (106) is comprised of a small, braided vasoocclusive element (108). This braided element (108) is typically a tubular element made completely or partially of regularly or randomly included radiopaque wires. The braid may optionally be partially woven of, or co-woven with, radiolucent fibers or wires. The braided member may be woven using known weaving techniques and devices to form the tubular member (108) shown in FIG. 5. The wire or fibers used in the production of the braid will typically be fairly small, e.g., in the range of 0.0005 to 0.0015 inches. The resulting woven braid diameter will normally be 0.008 to 0.018 inches. The braid structure is typically not as compliant as is that of, the coil. Consequently, a more ductile material such as platinum may be preferable in such a device. Additionally, the braid structure permits introduction of fibrous materials such as Dacron and the other filaments noted above which promote formation of a thrombus.

The fibrous elements incorporated into the braid may be a bundle of individual fibers, e.g., between 5 and 100 fibers per fibrous bundle, preferably 20–30 fibers per bundle, or may be monofilaments.

As was noted above, it may be desirable in certain circumstances to add fibrous materials outlying the vasoocclusive core so to provide additional bulk and area for creation of emboli.

The braided device (106) shown in FIG. 5 may be ovoid or of a deformed spherical shape as was the case with each of the devices described above. By the term "distorted" or "deformed" spherical shape, we mean a shape which includes spherical as well as shapes such as ovate or ovoid, but in any event having two orthogonal cross sections which are closed shapes having no straight sides.

Figure 6:
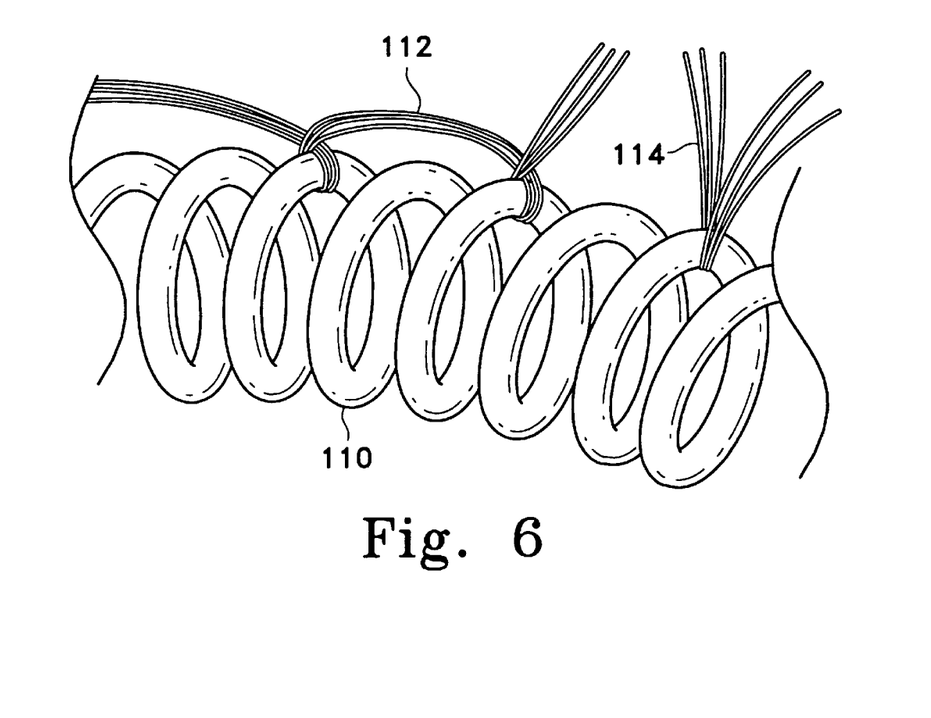
FIG. 6 shows a magnified section of a helical coil as could be used-in the inventive device having filamentary material attached through the loop of the device.

FIG. 6 shows a magnified side view of a portion of vasoocclusive coil (110) as may be used in the variations of the invention shown in FIGS. 1–4. Attached to the vasoocclusive coil (110) are two distinct methods of attaching fibrous materials to coil (110). First is a series of looping fibers (112), which are looped through or tied to coil (110) and continue axially down the coil. Another variation is the tuft (114) shown tied or otherwise affixed to coil (110). Tufts (114) are tied at multiple sites through the coil (110) so to provide a vast area of embolus forming sites.

Figure 7:
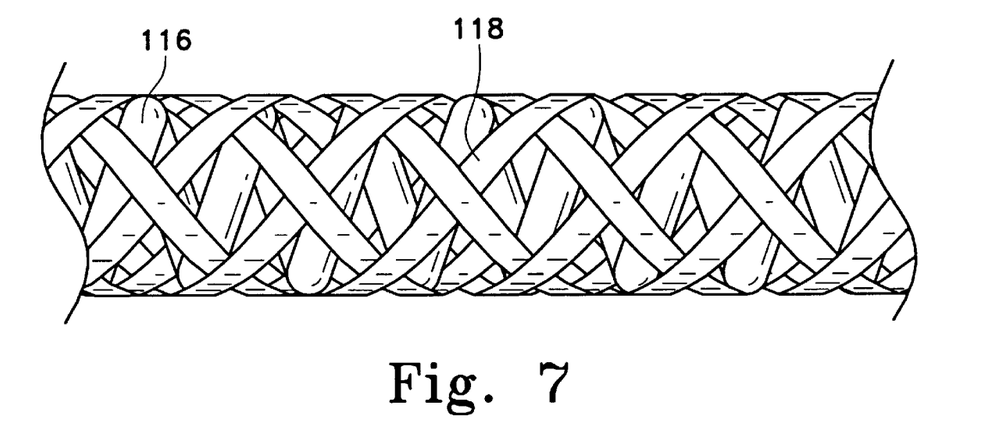
FIG. 7 shows a combination device in which the member is an inner metallic coil covered by an outer fibrous braided covering.

FIG. 7 shows still another variation and method for increasing the embolism-forming capability and rate of the device. FIG. 7 shows an embolic, helically shaped coil (116) covered by a fibrous braid (118). The method for producing the variation shown in FIG. 6 is described in U.S. Pat. Nos. 5,226,911 and 5,304,194 to Chee. The manner of producing the variation shown in FIG. 7 is described in U.S. Pat. No. 5,382,259, to Phelps and Van. The manner of making a co-woven braid using radiopaque fibers is shown in U.S. patent application No. 08/005,478, filed Jan. 15, 1993, to Engelson and Samson. Each of these techniques may be used in making the vasoocclusive devices described herein.

Figure 8:
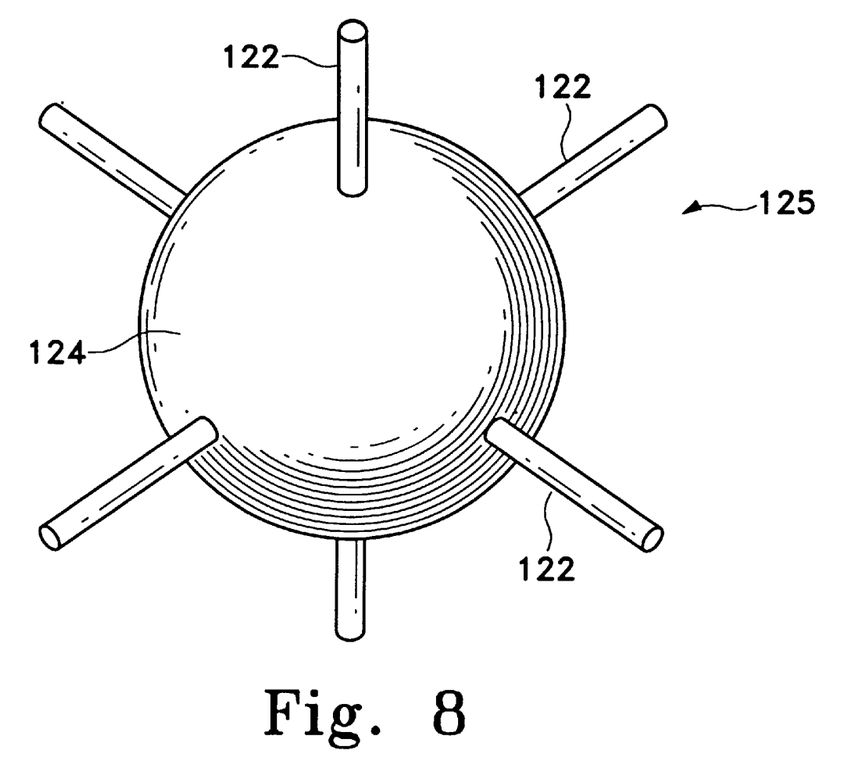
FIG. 8 shows a mandrel suitable for winding upon and heat-treating any device made according to the invention.

FIG. 8 depicts a mandrel suitable for making a spherical-shaped vasoocclusive device. The mandrel consists of three small metallic rods (122) and a core (124). The core is typically made of some refractory material such as alumina or zirconia or alumina-zirconia (for heat-treating devices made of purely metallic components or may be made of a ball of a metallic coil material). The function of core (104) is simply to form a support for winding, not pollute the device during the heat-treatment step to be described below, and provide a specific form to the device during that heat-treatment step.

Typically, the coil or braid is wound in the shape found in FIGS. 1–5 onto the core (124) found in FIG. 8. The core may instead be a distorted spherical shape, e.g., egg-shaped. It is held in place at the end of the wrapping step by simply winding the vasoocclusive element about one of the metallic rods (122).

If the entire then-wound device is metallic, it may be placed in an oven at an appropriate temperature to "set" the form of the device. If the device is a platinum alloy or of nitinol, such an appropriate 30 temperature is 1100° F. for 4 hours to provide a modest amount of preshaping to the resulting vasoocclusive device. After cooling, the device is removed from the core (124) and any filamentary material then attached. The vasoocclusive device is then placed in a cannula or catheter for delivery ultimately into a selected body cavity.

Should the make-up of the vasoocclusive element not be solely metal—in that it contains readily meltable plastic or the like—the temperature at which the heat treatment takes place is significantly lower and typically for a significantly shorter period of time. The flexural modulus of most plastics being significantly lower than those of metals, the bulk of the polymer-based device will be significantly larger than that of the metal-based device.

Figure 9:
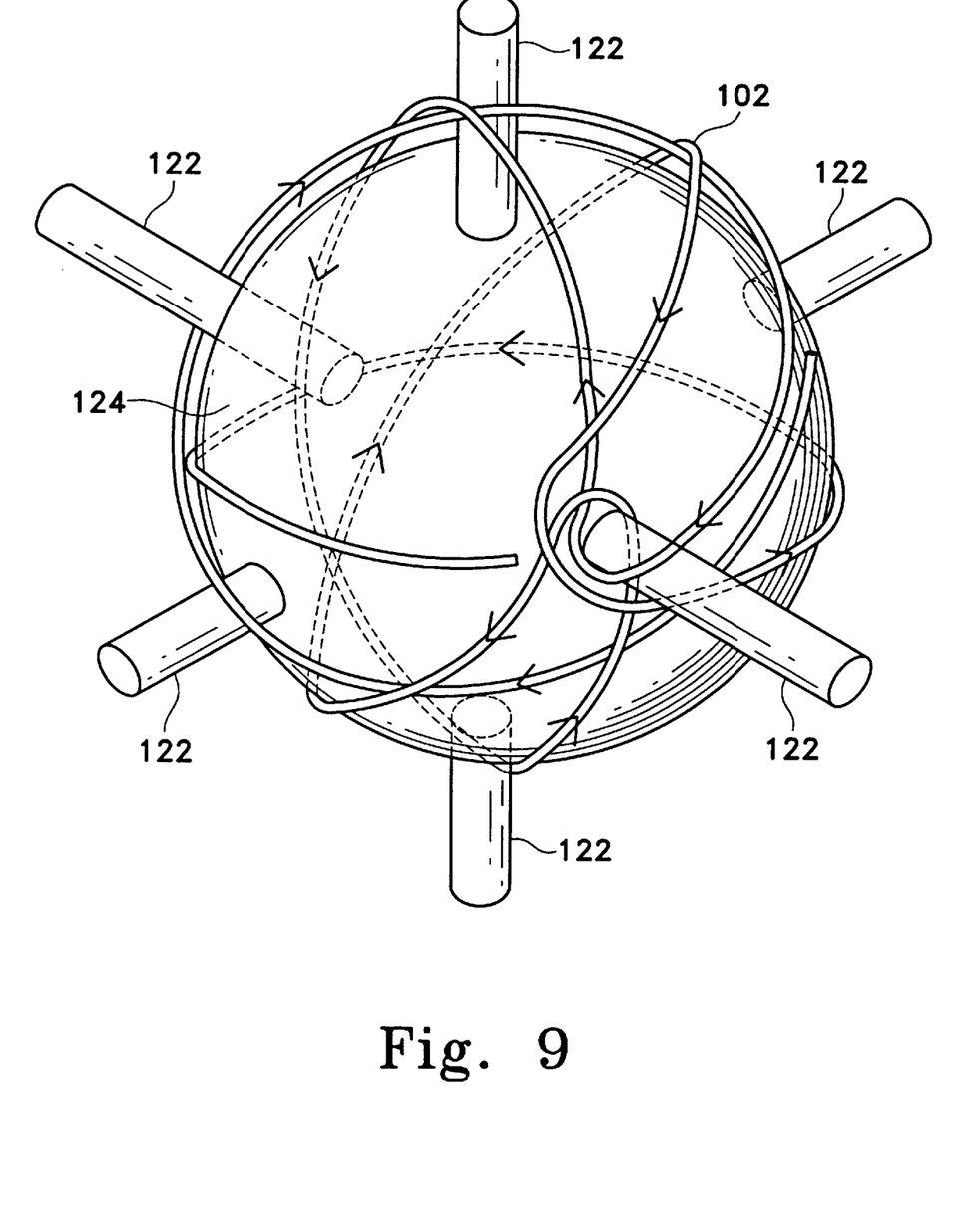
FIG. 9 shows a procedure for using the FIG. 8 mandrel for producing the FIG. 1 and 2 vasoocclusive device.

FIG. 9 shows a shadowed mandrel (125) made according to the FIG. 8 discussion which depicts the procedure for wrapping a primary coil (102) around the rods (122) in a sequence which results in the secondary spheroidal shape shown in FIGS. 1 and 2. The procedure for wrapping of the mandrel (125) may be followed from the point marked "start" through a series of turns (respectively 0°, 45°, 90°, 135°) to form the spheroid.

Figure 10:
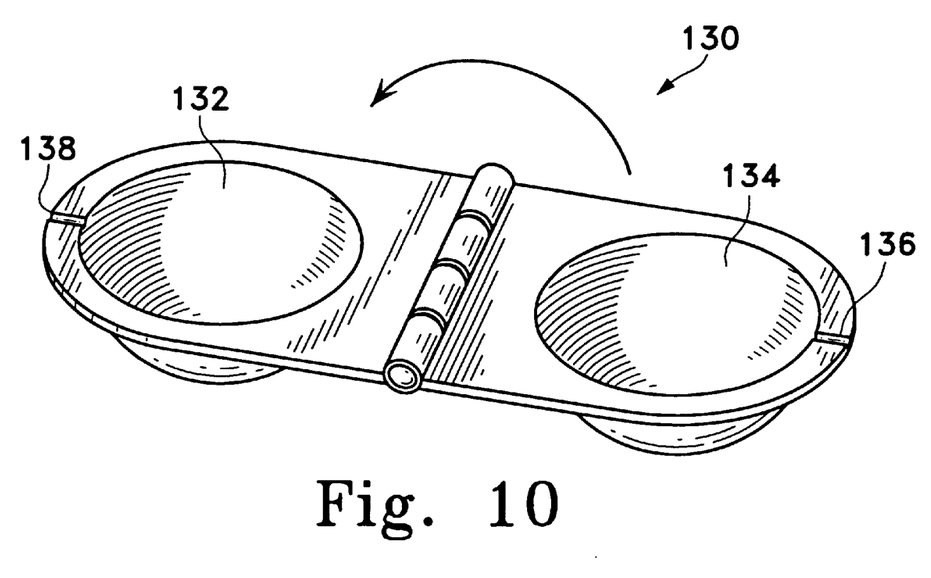
FIG. 10 shows an alternative mold suitable for shaping a section of vasoocclusive member during heat-treating so to produce a final spheroid shape.

FIG. 10 shows a "candy mold"—type device for rendering a shape to the inventive devices. The mold shown in FIG. 9 is typically of metallic composition so to allow it to be placed in an oven along with its contents. The way in which this device operates is somewhat more random than that shown in FIG. 8. The two halves of mold (130) close to form a cavity having a shape and size similar to the aneurysm into which the vasoocclusive device is to be placed. The left-hand cavity may be seen in (132); the right-hand cavity may be seen in (134). In this variation is a small slot (136) and (138) formed at the seam of device (130). After closing heat-treating device (130) in the manner shown by the arrow, a small opening made up of slots (136) and (138) may be seen from the outside. A length of previously wound or braided vasoocclusive member is fed in through that opening. Again, except for the very ends of the member inserted through the hole of (136) and (138), the majority of the member will lay against the interior wall of mold (130). Again, if the vasoocclusive device is to be produced from only a metal, the mold, with its included vasoocclusive member, is introduced into an oven for heat treatment at an appropriate temperature and for an appropriate time, such as discussed above.

Practitioners in this medical device area will undoubtedly have other ways of producing the noted anatomically shaped vasoocclusive devices.

The vasoocclusive devices of this invention may be used in a manner similar to those methods described in U.S. Pat. No. 4,994,069. Briefly, the inventive devices are typically to be supplied in a prepackaged form in a sterile cannula which is adapted to engage the proximal end of a catheter. Once the catheter is in place within a vessel and the distal end of the catheter is placed into, e.g., a mouth of an aneurysm, the vasoocclusive device is inserted into the aneurysm, where it assumes its relaxed shape. Although the device may be used with a flexible pusher without connection to the vasoocclusive device described here, much more desirable is the use of a mechanically detachable coupling on the vasoocclusive device and the pusher. Any of the mechanically detachable couplings described above in the Background of the Prior Art would be suitable in this instance. The methodology described by Guglielmi described above is also suitable.

It is within the scope of this invention that procedures for incorporating first the cage-like devices of this invention into an aneurysm or other vascular cavity be followed by introduction of other vasoocclusive devices such as coils or braid into the center of these cages to produce fine physical stability. Especially useful would be the shaped coils shown in Ritchart et al. discussed above or the ultrasoft embolism coils described in U.S. patent application 07/958,320, filed Nov. 18, 1992, to Berenstein.

EXAMPLE 1

We produced a series of spherical coils having outside diameters of 4 mm, 6 mm, 8 mm, and 10 mm from a primary coil winding which in turn was produced from 0.004" platinum wire wound over a 0.007" OD mandrel with no spacing between the coil turns. The outside diameter of the primary coil was therefore 0.015". The 0.004" diameter wire was chosen for optimum flexibility; coils of the noted size had been previously built with 0.003" platinum wire and they were not able to maintain their spherical shape after deployment. The coils were wound into spherical shapes using the procedure discussed with respect to FIG. 10 and annealed at a temperature of 1100° F. for four hours.

Figure 11:
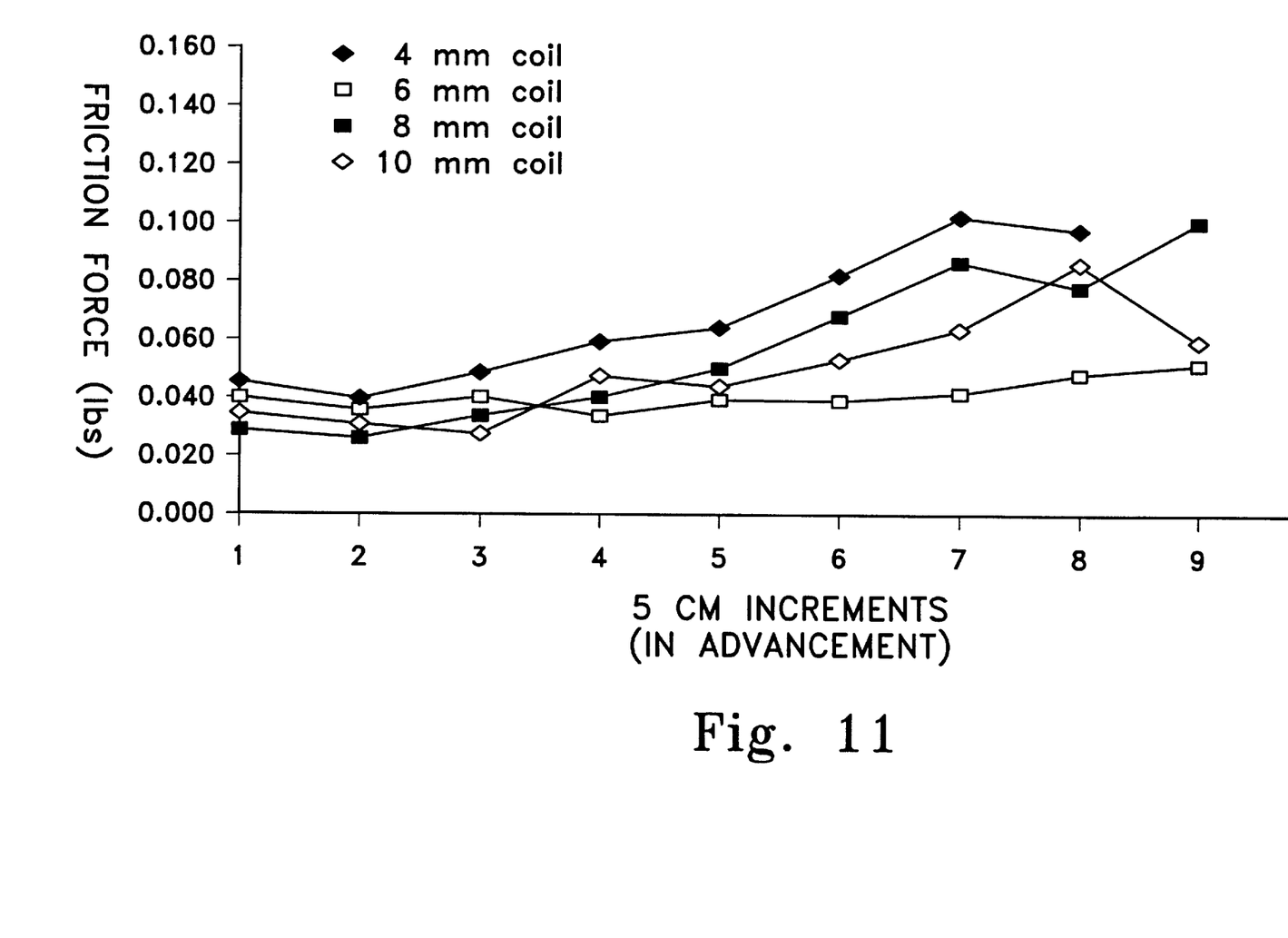
FIG. 11 is a graph depicting friction of the inventive device against a standardized catheter wall during deployment.

We pushed three of each of these coils through a Target Therapeutics TRACKER-18 catheter (150 cm total length with an inner diameter of 0.021") which had been strung through a tortuous path of five turns variously around three 1" diameter pins and two 0.5" pins. The coils were pushed to a starting position approximately 25 cm from the distal end of the catheter. A saline flush was then begun. The force needed to push the each of the coils for increments of 5 cm was then measured. The results of this testing is shown in FIG. 11. Each of the coils reflected an acceptable level of resistance in deployment. Each of the coils maintained a spherical shape upon ejection from the catheter.

EXAMPLE 2

We constructed a transparent, elastic, polymeric model, each with two rows of lateral wall aneurysms for comparison—two each at diameters of 10, 8, 6, and 4 millimeters. One row had narrow necks (less than 50% of aneurysm diameter), the other had wide necks (greater than 50% of aneurysm diameter). The model was perfused both with Newtonian and with non-Newtonian fluids flowing at physiologic volumes and pulse profiles. We injected isobaric dyes and observed the flow dynamics. We then delivered various sizes and kinds of coils to each of the aneurysms and observed changes in flow dynamics.

We observed that the angular velocities within the aneurysm varied inversely with aneurysm diameter. That is to say that smaller aneurysms had a faster angular flow velocities. We also observed that aneurysms with wider necks had more rapid peripheral flow than those with smaller necks. Surprisingly, both small-neck aneurysms and wide-neck aneurysms were observed to have high angular flow velocities. Spherical coils introduced into the aneurysms markedly decreased the angular velocity by creating internal friction or by insulating the fluid in the aneurysm from that section of the parent artery.

The coils made from 0.004-inch platinum wire remained stable within the small aneurysms. In larger aneurysms, especially those with wide necks, greater hoop strength seemed desirable for physical stability within the aneurysm.

Modification of the above-described variations for carrying out the invention which are obvious to those of ordinary skill in the fields of medical device design generally, and vasoocclusive devices specifically, are intended to be within the scope of the following claims.

We claim as our invention:

1. A method for producing a three dimensional vasoocclusive member, comprising the steps of:
   preparing a generally linear primary coil element;
   winding said primary coil element onto a mandrel having a spherical or distorted spherical exterior surface, said winding includes winding said primary element around a plurality of elongate members extending from said mandrel exterior surface; and
   heating said mandrel and said primary coil element to produce said three dimensional member, said three dimensional member being self-forming into the spherical or distorted spherical form.

2. The method of claim 1, further comprising the step of:
   attaching polymeric fibers to said primary element after said heating step.

3. The method of claim 2, said polymeric fibers comprises one or more bundles of polymeric fibers, said attaching step includes looping or affixing each of said bundles to a plurality of locations on said primary element.

4. The method of claim 2, said polymeric fibers comprises a plurality of tufts of fibers, said attaching step includes affixing each of said tufts to a respective location on said primary element.

5. The method of claim 1, wherein said primary coil element is covered by an outer braid.

6. The method of claim 1, wherein said mandrel comprises a refractory material selected from alumina, zirconia, and alumina-zirconia.

7. The method of claim 1, wherein said winding around the elongate members follows a sequence of turns at angles selected from 0°, 45°, 90° and 135° to form said spherical or distorted spherical form.

8. The method of claim 1 where the primary element comprises a material selected from stainless steels, platinum, palladium, rhodium, gold, tungsten, silver, tantalum, and alloys of platinum, palladium, rhodium, gold, tungsten, silver, and/or tantalum.

9. The method of claim 8, where the primary element comprises an alloy of platinum and tungsten.

10. The method of claim 1 where the primary element comprises radiolucent fibers or polymers.

11. The method of claim 10 where said radiolucent fibers or polymers are selected from polyesters, polyglycolic acid, polylactic acid, fluoropolymers, polyamides, and silk.

12. The method of claim 10 where the primary element further comprises a radiopaque filler.

13. The method of claim 12 where the radiopaque filler comprises a material selected from powdered tantalum, powdered tungsten, bismuth oxide, and barium sulfate.

14. A three dimensional coil member formed by the method comprising the steps of:

preparing a generally linear primary coil element;

winding said primary coil element onto a mandrel having a spherical or distorted spherical exterior surface, said winding includes winding said primary coil element around a plurality of elongate members extending from said mandrel exterior surface; and heating said mandrel and said primary element to produce said three dimensional member, said three dimensional member being self-forming into the spherical or distorted spherical form.

15. The three dimensional coil member of claim 14, wherein said winding around the elongate members follows a sequence of turns selected from the group consisting of 0°, 45°, 90° and 135° to form said spherical or distorted spherical form.

16. The three dimensional product of claim 14, where the primary element comprises an alloy of platinum and tungsten.

17. A method for producing a three dimensional vasoocclusive member, comprising the steps of:

preparing a generally linear primary coil element;

inserting said primary coil element into a shape forming member having an internal spherical or distorted spherical form; and heating said shape forming member and said primary coil element to produce said three dimensional member, said three dimensional member being self-forming into the spherical or distorted spherical form.

18. The method of claim 17, said shape forming member having two sections closeable to form a spherical cavity or distorted spherical cavity therein and an opening through at least one of said sections, said inserting step comprises the step of inserting said primary element through said opening into said cavity.

19. The method of claim 18, after said heating step, further comprising the steps of:

opening said shape forming member and removing said three dimensional member from said shape forming member; and attaching polymeric fibers to said primary element.

20. The method of claim 19, said polymeric fibers comprises one or more bundles of polymeric fibers, said attaching step includes looping or affixing each of said bundles to a plurality of locations on said primary element.

21. The method of claim 19, said polymeric fibers comprises a plurality of tufts of fibers, said attaching step includes affixing each of said tufts to a respective location on said primary element.

22. The method of claim 17, wherein said primary coil element is further covered by an outer braid.

23. The method of claim 17 where the primary element comprises a material selected from stainless steels, platinum, palladium, rhodium, gold, tungsten, silver, tantalum, and alloys of platinum, palladium, rhodium, gold, tungsten, silver, and/or tantalum.

24. The method of claim 23 where the primary element comprises an alloy of platinum and tungsten.

25. The method of claim 17 where the primary element comprises radiolucent fibers or polymers.

26. The three dimensional product formed by the method comprising the steps of:

preparing a generally linear primary coil element;

inserting said primary element into a shape forming coil member having an internal spherical or distorted spherical form; and heating said shape forming member and said primary element to produce said three dimensional member, said three dimensional member being self-forming into the spherical or distorted spherical form.

27. The three dimensional product of claim 26, said shape forming member having two sections closeable to form a spherical cavity or distorted spherical cavity therein and an opening through at least one of said sections, said inserting step comprises the step of inserting said primary element through said opening into said cavity.

28. The three dimensional product of claim 26, where the primary element comprises an alloy of platinum and tungsten.

* * * * *